US011058297B2

(12) United States Patent
Schmoll

(10) Patent No.: US 11,058,297 B2
(45) Date of Patent: Jul. 13, 2021

(54) 1060 NM WAVELENGTH RANGE-BASED OPTICAL COHERENCE TOMOGRAPHY (OCT) SYSTEM FOR ANTERIOR/POSTERIOR SEGMENT IMAGING OF AN EYE

(71) Applicants: Carl Zeiss Meditec, Inc., Dublin, CA (US); Carl Zeiss Meditec AG, Jena (DE)

(72) Inventor: Tilman Schmoll, Vienna (AT)

(73) Assignees: CARL ZEISS MEDITEC, INC., Dublin, CA (US); CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 16/330,355

(22) PCT Filed: Sep. 28, 2017

(86) PCT No.: PCT/EP2017/074706
§ 371 (c)(1),
(2) Date: Mar. 4, 2019

(87) PCT Pub. No.: WO2018/060375
PCT Pub. Date: Apr. 5, 2018

(65) Prior Publication Data
US 2019/0216313 A1  Jul. 18, 2019

Related U.S. Application Data

(60) Provisional application No. 62/401,607, filed on Sep. 29, 2016.

(51) Int. Cl.
*A61B 3/10* (2006.01)
*A61B 3/00* (2006.01)
*A61B 3/14* (2006.01)

(52) U.S. Cl.
CPC ............ *A61B 3/102* (2013.01); *A61B 3/0008* (2013.01); *A61B 3/14* (2013.01); *A61B 3/0016* (2013.01)

(58) Field of Classification Search
CPC ........... A61B 3/14; A61B 3/0025; A61B 3/12; A61B 3/102; A61B 3/0058
(Continued)

(56) References Cited

U.S. PATENT DOCUMENTS 7,648,242 B2 * 1/2010 Ferguson ........... G01B 9/02044
351/221
9,332,902 B2  5/2016 Tumlinson et al.
(Continued)

FOREIGN PATENT DOCUMENTS

CN    102670172 B    4/2015
JP    2009503519 A    1/2009
(Continued)

OTHER PUBLICATIONS

Blazkiewicz et al., "Signal-To-Noise Ratio Study of Full-Field Fourier-Domain Optical Coherence Tomography", Applied Optics, vol. 44, No. 36, Dec. 20, 2005, pp. 7722-7729.
(Continued)

*Primary Examiner* — Mohammed A Hasan
(74) *Attorney, Agent, or Firm* — Morrison & Foerster LLP

(57) ABSTRACT

An OCT system for generating images of an anterior or posterior segment of an eye is described. The system includes a light source, a controller, optics, a detector, and a processor. The light source generates a beam of light and is capable of operating in a posterior or an anterior segment imaging mode. In the posterior segment imaging mode, light source outputs light with a first spectral bandwidth of less than 120 nm and including wavelengths between about 1060
(Continued)

to 1070 nm. In the anterior segment imaging mode the light source outputs light with a second spectral bandwidth that is larger than 120 nm. The controller enables switching between the posterior or anterior segment imaging mode.

16 Claims, 6 Drawing Sheets

(58) Field of Classification Search
USPC .......................................................... 351/206
See application file for complete search history.

(56) References Cited

U.S. PATENT DOCUMENTS

| | | | |
|---|---|---|---|
| 2007/0291277 A1 | 12/2007 | Everett et al. | |
| 2012/0083667 A1 | 4/2012 | Isogai et al. | |
| 2013/0100456 A1* | 4/2013 | Yu | G01B 9/02082 356/479 |
| 2013/0163003 A1* | 6/2013 | Massow | G01B 9/02091 356/479 |
| 2014/0268038 A1* | 9/2014 | Schmoll | A61B 3/102 351/206 |
| 2016/0000320 A1* | 1/2016 | Sharma | G01B 9/02044 351/206 |
| 2016/0166144 A1 | 6/2016 | Izatt et al. | |

FOREIGN PATENT DOCUMENTS

| | | |
|---|---|---|
| JP | 2011027715 A | 2/2011 |
| JP | 2011528801 A | 11/2011 |
| JP | 2012075640 A | 4/2012 |
| JP | 2013217700 A | 10/2013 |
| WO | WO-2007016296 A2 | 2/2007 |

OTHER PUBLICATIONS

Coello et al., "Group-Velocity Dispersion Measurements of Water, Seawater, and Ocular Components using Multiphoton Intrapulse Interference Phase Scan", Applied Optics, vol. 46, No. 35, Dec. 10, 2007, pp. 8394-8401.

Danielson et al., "Absolute Optical Ranging using Low Coherence Interferometry", Applied Optics, vol. 30, No. 21, Jul. 20, 1991, pp. 2975-2979.

Drexler et al., "In Vivo Ultrahigh-Resolution Optical Coherence Tomography", Optics Letters, vol. 24, No. 17, Sep. 1, 1999, pp. 1221-1223.

Drexler et al., "State-of-the-Art Retinal Optical Coherence Tomography", Progress in Retinal and Eye Research, vol. 27, 2008, pp. 45-88.

Hariri et al., "Limiting Factors to the OCT Axial Resolution for In-Vivo Imaging of Human and Rodent Retina in the 1060nm Wavelength Range", Optics Express, vol. 17, No. 26, Dec. 21, 2009, pp. 24304-24316.

Hillman et al., "The Effect of Water Dispersion and Absorption on Axial Resolution in Ultrahigh-Resolution Optical Coherence Tomography", Optics Express, vol. 13, No. 6, Mar. 21, 2005, pp. 1860-1874.

Hillmann et al., "Holoscopy-Holographic Optical Coherence Tomography", Optics Letters, vol. 36, No. 13, Jul. 1, 2011, pp. 2390-2392.

Huber et al., "Fourier Domain Mode Locking at 1050 nm for Ultra-High-Speed Optical Coherence Tomography of the Human Retina at 236,000 Axial Scans Per Second", Optics Letters, vol. 32, No. 14, Jul. 15, 2007, pp. 2049-2051.

International Preliminary Report on Patentability received for PCT Patent Application No. PCT/EP2017/074706, dated Apr. 11, 2019, 8 pages.

International Search Report and Written Opinion received for PCT Application No. PCT/EP2017/074706, dated Jan. 8, 2018, 13 pages.

Klein et al., "Megahertz OCT for Ultrawide-Field Retinal Imaging with a 1050nm Fourier Domain Mode-Locked Laser", Optics Express, vol. 19, No. 4, Feb. 14, 2011, pp. 3044-3062.

Kuznetsov et al., "Compact Ultrafast Reflective Fabry-Perot Tunable Lasers for OCT Imaging Applications", Proc. of SPIE, vol. 7554, 2010, pp. 75541F-1-75541F-6.

Lee et al., "Optimization for Axial Resolution, Depth Range, and Sensitivity of Spectral Domain Optical Coherence Tomography at 1.3 um", Journal of the Korean Physical Society, vol. 55, No. 6, Dec. 2009, pp. 2354-2360.

Marschall et al., "Broadband Fourier Domain Mode-Locked Laser for Optical Coherence Tomography at 1060 nm", Proceedings of the SPIE, vol. 8213, 2012, 3 pages.

Marschall et al., "Fourier Domain Mode-Locked Swept Source at 1050 nm based on a Tapered Amplifier", Optics Express, vol. 18, No. 15, Jul. 19, 2010, pp. 15820-15831.

Marschall et al., "Investigation of the Impact of Water Absorption on Retinal OCT Imaging in the 1060 nm Range", Biomedical Optics Express, vol. 3, No. 7, Jul. 1, 2012, pp. 1620-1631.

Nakamura et al., "High-Speed Three-Dimensional Human Retinal Imaging by Line-Field Spectral Domain Optical Coherence Tomography", Optics Express, vol. 15, No. 12, Jun. 11, 2007, pp. 7103-7116.

Palmer et al., "Optical Properties of Water in the Near Infrared", Journal of the Optical Society of America, vol. 64, No. 8, Aug. 1974, pp. 1107-1110.

Potsaid et al., "Ultrahigh Speed Spectral / Fourier Domain OCT Ophthalmic Imaging at 70,000 to 312,500 Axial Scans Per Second", Optics Express, vol. 16, No. 19, Sep. 15, 2008, pp. 15149-15169.

Považay et al., "Enhanced Visualization of Choroidal Vessels using Ultrahigh Resolution Ophthalmic OCT at 1050 nm", Optics Express, vol. 11, No. 17, Aug. 25, 2003, pp. 1980-1986.

Unterhuber et al., "In Vivo Retinal Optical Coherence Tomography at 1040 nm Enhanced Penetration into the Choroid", Optics Express, vol. 13, No. 9, May 2, 2005, pp. 3252-3258.

Van Den Berg et al., "Near Infrared Light Absorption in the Human Eye Media", Vision Research, vol. 37, No. 2, 1997, pp. 249-253.

Wang et al., "Optimal Wavelength for Ultrahigh-Resolution Optical Coherence Tomography", Optics Express, vol. 11, No. 12, Jun. 16, 2003, pp. 1411-1417.

Wolbarsht et al., "Melanin, A Unique Biological Absorber", Applied Optics, vol. 20, No. 13, Jul. 1, 1981, pp. 2184-2186.

Yasuno et al., "In Vivo High-Contrast Imaging of Deep Posterior Eye by 1-μm Swept Source Optical Coherence Tomography and Scattering Optical Coherence Angiography", Optics Express, vol. 15, No. 10, May 14, 2007, pp. 6121-6139.

Japanese Search Report received for Japanese Patent Application No. 2019-511748, dated Mar. 9, 2021, 19 pages. (English translation p. 1-11, Original copy p. 12-19).

Office Action received for Japanese Patent Application No. 2019-511748, drafted on Apr. 21, 2021, 8 pages. (English translation p. 1-4, Original copy p. 5-8).

* cited by examiner

1060 NM WAVELENGTH RANGE-BASED OPTICAL COHERENCE TOMOGRAPHY (OCT) SYSTEM FOR ANTERIOR/POSTERIOR SEGMENT IMAGING OF AN EYE

PRIORITY

The present application is a National Phase application under 35 U.S.C. § 371 of International Application No. PCT/EP2017/074706, filed Sep. 28, 2017, which claims priority to U.S. Provisional Application Ser. No. 62/401,607, filed Sep. 29, 2016, the contents of each of which are hereby incorporated by reference in their entirety.

BACKGROUND

Optical coherence tomography (OCT) is an optical imaging technology for performing in situ real-time cross-sectional imaging of tissue structures with micrometer resolution. OCT measures the scattering profile of a sample along the OCT beam. Each scattering profile is called an axial scan, or A-scan. Cross-sectional images, called B-scans, and by extension 3D volumes, are built up from many A-scans, with the OCT beam illuminating a set of transverse locations on the sample either by scanning or field illumination.

One of the prominent advantages of OCT is the high axial resolution in the micrometer or even submicrometer range. The axial resolution depends primarily on the spectral bandwidth of the used light source. The axial resolution is also influenced by chromatic dispersion and by spectrally dependent attenuation of any media that the probing light has to pass (see for example, B. L. Danielson and C. Y. Boisrobert, "Absolute optical ranging using low coherence interferometry," Appl. Opt. 30, 2975-2979 (1991); T. Hillman and D. Sampson, "The effect of water dispersion and absorption on axial resolution in ultrahigh resolution optical coherence tomography," Opt. Express 13, 1860-1874 (2005); S. Hariri, A. A. Moayed, A. Dracopoulos, C. Hyun, S. Boyd, and K. Bizheva, "Limiting factors to the OCT axial resolution for in-vivo imaging of human and rodent retina in the 1060 nm wavelength range," Opt. Express 17, 24304-24316 (2009), hereby incorporated by reference).

In the case of retinal imaging, the performance is, to a large extent, governed by the properties of water, the main constituent of the ocular media (see for example, T. J. van den Berg and H. Spekreijse, "Near infrared light absorption in the human eye media," Vis. Res. 37, 249-253 (1997); and Y. Coello, B. Xu, T. L. Miller, V. V. Lozovoy, and M. Dantus, "Group-velocity dispersion measurements of water, seawater, and ocular components using multiphoton intrapulse interference phase scan," Appl. Opt. 46, 8394-8401 (2007), hereby incorporated by reference). A double pass through the anterior eye segment and the vitreous body adds up to a path length of about 50 mm exhibiting wavelength-dependent dispersion and absorption (see for example, FIG. 1).

Most OCT systems for retinal imaging operate at a center wavelength in the 800 nm range, primarily due to negligible absorption by water (see for example, W. Drexler and J. G. Fujimoto, "State-of-the-art retinal optical coherence tomography," Prog. Retin. Eye Res. 27, 45-88 (2008), hereby incorporated by reference). Furthermore, well developed broadband light sources are available, e.g., titanium:sapphire short-pulse lasers, which offer ultra-high axial resolution (see for example, W. Drexler, U. Morgner, F. X. Kartner, C. Pitris, S. A. Boppart, X. D. Li, E. P. Ippen, and J. G. Fujimoto, "In vivo ultrahigh-resolution optical coherence tomography," Opt. Lett. 24, 1221-1223 (1999), hereby incorporated by reference). Silicon detector arrays with large pixel numbers enable the implementation of fast spectrometer-based Fourier domain OCT (FD-OCT) systems (see for example, B. Potsaid, I. Gorczynska, V. J. Srinivasan, Y. Chen, J. Jiang, A. Cable, and J. G. Fujimoto, "Ultrahigh speed spectral/Fourier domain OCT ophthalmic imaging at 70,000 to 312,500 axial scans per second," Opt. Express 16, 15149-15169 (2008), hereby incorporated by reference).

During the past few years, the wavelength range around 1060 nm, where water absorption has a local minimum (see FIG. 1), found increasing interest for imaging the retina and the underlying choroid (see for example, B. Povazay, K. Bizheva, B. Hermann, A. Unterhuber, H. Sattmann, A. F. Fercher, W. Drexler, C. Schubert, P. K. Ahnelt, M. Mei, R. Holzwarth, W. J. Wadsworth, J. C. Knight, and P. S. J. Russel, "Enhanced visualization of choroidal vessels using ultrahigh resolution ophthalmic OCT at 1050 nm," Opt. Express 11, 1980-1986 (2003); A. Unterhuber, B. Povazay, B. Hermann, H. Sattmann, A. Chavez-Pirson, and W. Drexler, "In vivo retinal optical coherence tomography at 1040 nm—enhanced penetration into the choroid," Opt. Express 13, 3252-3258 (2005); Y. Yasuno, Y. Hong, S. Makita, M. Yamanari, M. Akiba, M. Miura, and T. Yatagai, "In vivo high-contrast imaging of deep posterior eye by 1-µm swept source optical coherence tomography and scattering optical coherence angiography," Opt. Express 15, 6121-6139 (2007), hereby incorporated by reference).

In the wavelength range around 1060 nm, attenuation by melanin is lower (see for example, M. L. Wolbarsht, A. W. Walsh, and G. George, "Melanin, a unique biological absorber," Appl. Opt. 20, 2184-2186 (1981), hereby incorporated by reference), hence more light is transmitted through the retinal pigment epithelium (RPE). Reduced scattering at higher wavelengths generally enables deeper penetration into the tissue, and it is beneficial for imaging in eyes affected by cataracts. Furthermore, chromatic dispersion in water is low around 1000 nm, which helps in maintaining a high axial resolution (see for example, Y. Wang, J. S. Nelson, Z. Chen, B. J. Reiser, R. S. Chuck, and R. S. Windeler, "Optimal wavelength for ultrahighresolution optical coherence tomography," Opt. Express 11, 1411-1417 (2003), hereby incorporated by reference).

For wavelengths above 1000 nm, OCT systems usually utilize wavelength-swept laser light sources, so-called swept sources, rather than broadband light sources and spectrometers, because available detector arrays based on indium gallium arsenide are significantly more expensive than their silicon counterparts. Swept-source OCT can provide long ranging depths and ultra-high image acquisition speed, and it is more robust against motion artifacts. Continuing research therefore focuses on the development of high-performance swept sources for the 1060 nm range (see for example, T. Klein, W. Wieser, C. M. Eigenwillig, B. R. Biedermann, and R. Huber, "Megahertz OCT for ultrawidefield retinal imaging with a 1050 nm Fourier domain modelocked laser," Opt. Express 19, 3044-3062 (2011); R. Huber, D. C. Adler, V. J. Srinivasan, and J. G. Fujimoto, "Fourier domain mode locking at 1050 nm for ultrahigh-speed optical coherence tomography of the human retina at 236,000 axial scans per second," Opt. Lett. 32, 2049-2051 (2007); M. Kuznetsov, W. Atia, B. Johnson, and D. Flanders, "Compact ultrafast reflective Fabry-Perot tunable lasers for oct imaging applications," Proc. SPIE 7554, 75541F (2010); S. Marschall, T. Klein, W. Wieser, B. R. Biedermann, K. Hsu, K. P. Hansen, B. Sumpf, K.-H. Hasler, G. Erbert, O. B. Jensen, C. Pedersen, R. Huber, and P. E. Andersen, "Fourier domain mode-locked swept source at 1050 nm based on a tapered amplifier," Opt. Express 18, 15820-15831 (2010); and S. Marschall, T. Klein, W. Wieser, T. Torzicky, M. Pircher, B. R. Biedermann, C. Pedersen, C. K. Hitzenberger, R. Huber, and P. E. Andersen, "Broadband Fourier domain mode-locked laser for optical coherence tomography at 1060 nm," Proc. SPIE 8213, 82130R (2012), each of which are hereby incorporated by reference).

1060 nm swept sources are usually designed for a spectral sweep width of <110 nm. This value is derived from the width of the water absorption window. Due to the high absorption below 1000 nm and above 1100 nm (as shown in FIG. 1), larger bandwidths do not lead to a higher axial resolution when imaging the human retina. In fact, larger bandwidths would even lead to a loss in signal, because the optical power is measured in front of the eye and maximum exposure limits typically do not include water absorption variations to that level of spectral resolution.

The above makes sense when imaging the posterior segment of the eye. However, when imaging the anterior segment of the eye, one could make use of larger bandwidth 1060 nm sources in order to increase the axial resolution, because the light does not have to penetrate as much water. It would therefore be desirable for a system, which can image the retina and the anterior segment of the eye at different sweep widths to achieve an improved resolution.

SUMMARY

According to one aspect of the subject matter described in the present application, an optical coherence tomography (OCT) for generating images of an anterior or posterior segment of an eye includes a light source for generating a beam of light, said light source capable of operating in at least two imaging modes comprising a posterior segment imaging mode in which the light source outputs light with a first spectral bandwidth, and an anterior segment imaging mode in which the light source outputs light with a second spectral bandwidth that is larger than the first spectral bandwidth; a controller for switching between the posterior segment imaging mode and the anterior segment imaging mode; optics for scanning the generated light over a set of transverse locations across the anterior or posterior segment of the eye; a detector for measuring light returning from the eye and generating output signals in response thereto; and a processor for generating images of the anterior or posterior segment of the eye based on the output signals.

The above aspect may optionally include one or more features. For instance, the features include that the first spectral bandwidth is equal or narrower than the width of the 1060 nm water absorption window, that the second spectral bandwidth is larger than the width of the 1060 nm water absorption window, and that the light source is a swept laser light source.

The present invention is particularly advantageous in a number of respects. By way of example and not limitation, the invention enables 1060 nm posterior segment imaging with optimized sensitivity as well as high resolution anterior segment imaging of an eye using the same ophthalmic diagnostic device.

The features and advantages described herein are not all-inclusive and many additional features and advantages will be apparent to one of ordinary skill in the art in view of the figures and description. Moreover, it should be noted that the language used in the specification has been principally selected for readability and instructional purposes and not to limit the scope of the inventive subject matter.

DETAILED DESCRIPTION

All patent and non-patent references cited within this specification are herein incorporated by reference in their entirety to the same extent as if the disclosure of each individual patent and non-patent reference was specifically and individually indicated to be incorporated by reference in its entirety.

Example OCT System

Figure 2:
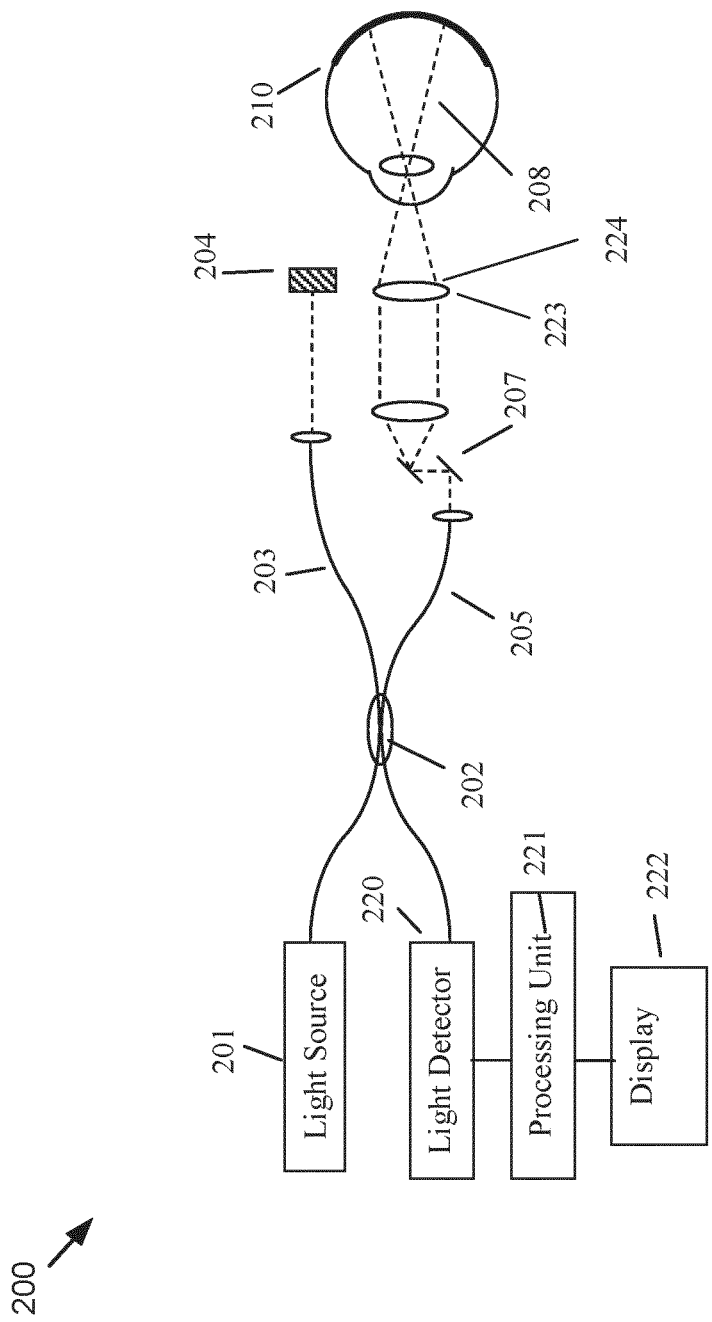
FIG. 2 is a generalized optical coherence tomography (OCT) system for anterior/posterior segment imaging of an eye according to one aspect of the present invention.

A generalized FD-OCT system used to collect 3-D image data of the eye suitable for use with the present invention is illustrated in FIG. 2. A FD-OCT system 200 includes a light source, 201, which can for example be a broadband light source with short temporal coherence length in the case of SD-OCT or a wavelength tunable laser source in the case of SS-OCT. The light source 201 is capable of switching between an anterior segment mode to image the anterior segment of the eye and a posterior segment mode to image the posterior segment of the eye, as discussed later below. This switching between the anterior segment mode and the posterior segment mode occurs using a controller, either incorporated as part of the source or as a separate element of the system (not shown). A beam of light from source 201 is routed, typically by optical fiber 205, to illuminate the sample 210, a typical sample being tissues in the human eye. The light is directed towards a region of the sample 210, typically with a scanner 207 between the output of the fiber and the sample, so that the beam of light (dashed line 208) is scanned laterally (in x and y) over the region of the sample to be imaged. Light scattered from the sample is collected, typically into the same fiber 205 used to route the light for illumination. Reference light derived from the same source 201 travels a separate path, in this case involving fiber 203 and retro-reflector 204 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 202, to form light interference in a detector 220. Although a single fiber port is shown going to the detector, those skilled in the art recognize that various designs of interferometers can be used for balanced or unbalanced detection of the interference signal. The output from the detector 220 is supplied to a processor 221 that converts the observed interference into depth information of the sample. The results can be stored in the processor 221 or other storage medium or displayed on display 222. The processing and storing functions may be localized within the OCT instrument or functions may be performed on an external processing unit (e.g., the computer system 300 as shown in FIG. 3) to which the collected data is transferred. This unit could be dedicated to data processing or perform other tasks which are quite general and not dedicated to the OCT device. The processor 221 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion.

The interference causes the intensity of the interfered light to vary across the spectrum. The Fourier transform of the interference signal reveals the profile of scattering intensities at different path lengths, and therefore scattering as a function of depth (z-direction) in the sample. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. A variety of ways to create B-scans are known to those skilled in the art including but not limited to along the horizontal or x-direction, along the vertical or y-direction, along the diagonal of x and y, or in a circular or spiral pattern.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—holographic optical coherence tomography" *Optics Letters* 36(13): 2390 2011; Y. Nakamura, et al, "High-Speed three dimensional human retinal imaging by line field spectral domain optical coherence tomography" *Optics Express* 15(12):7103 2007; Blazkiewicz et al, "Signal-to-noise ratio study of full-field Fourier-domain optical coherence tomography" *Applied Optics* 44(36):7722 (2005)). In time-domain systems, either the sample or reference arm needs to have a tunable optical delay to generate interference between reference light and light scattered at various depths within the sample. Balanced detection systems are typically used in TD-OCT and SS-OCT systems, while spectrometers are used at the detection port for SD-OCT systems.

In FIG. 2, lens (223) is normally called the objective or ocular lens. It is present to produce a focused beam onto a desired part of the eye. In order to accommodate anterior segment (cornea, aqueous humor, and crystalline lens) and posterior segment (vitreous humor and the various retinal tissues down to the sclera), the lens (223) needs to have its focal length adjusted. There is a variety of ways to achieve this, but often a method is to insert or add a negative lens at a position just downstream of its rear vertex (224). Such a lens could be added manually by the user and attached to the system via magnets or any other attachment mechanism known to one skilled in the art. Thus, in this particular approach, addition of this lens to the optical configuration of the system permits the instrument to switch between anterior and posterior imaging. In addition, the delay between the reference and sample arms is adjusted when switching between the two regions of the eye.

Commercial OCT devices have been developed in the past for imaging the anterior and/or posterior sections of the eye. Some of these are, for example, Zeiss Cirrus™ HD-OCT, Visante™ Omni, and Stratus™ (Carl Zeiss Meditec, Inc. Dublin, Calif.)). The Cirrus™ HD-OCT system allows for imaging both the anterior and posterior regions by inserting a lens in the beampath to change the focal properties of the system and adjusting the delay line between the sample and reference arms as described in US Publication No. 2007/0291277. The Cirrus™ HD-OCT produces images of the anterior segment of an eye using spectral domain optical coherence tomography (SD-OCT) technology.

1060 nm Wavelength Range-Based OCT System for Anterior/Posterior Segment Imaging As discussed in the background section of the present disclosure, in the 1060 nm wavelength band, one can only achieve approximately 6 μm axial resolution in the retina because only a spectral band of approximately 100 nm passes through the vitreous and back without being heavily attenuated. Because 1060 nm swept sources are mainly used for posterior segment imaging, the swept sources are usually designed for a 100-110 nm spectral width, centered around 1060 nm. The anterior segment could however be imaged at a much higher resolution, because the light does not have to penetrate as much water. It is therefore desirable to design an OCT system, which can switch its spectral width to match the water absorption window when imaging the posterior segment, but increases its spectral bandwidth when imaging the anterior segment.

In a preferred embodiment of the present application, the OCT system of FIG. 2 includes a swept laser light source 201, which is capable of operating in at least two modes: a posterior segment imaging mode with a spectrum optimized for the 1060 nm water absorption window, and an anterior segment imaging mode with a spectrum wider than the 1060 nm water absorption window. Specifically, in this embodiment, the light source 201 of the OCT system 200 is configured in a way such that in the posterior segment imaging mode, the light source 201 outputs light with a spectral bandwidth equal to or narrower than the width of the 1060 nm water absorption window, and in the anterior segment imaging mode, the light source 201 outputs light with a spectral bandwidth larger than the width of the 1060 nm water absorption window. The switching between the anterior segment imaging mode and the posterior segment imaging mode may occur using a controller, in some cases an optical switch.

The advantage of such a OCT system is that it enables 1060 nm posterior segment imaging with optimized sensitivity as well as high resolution anterior segment imaging of an eye using the same OCT system.

Figure 1:
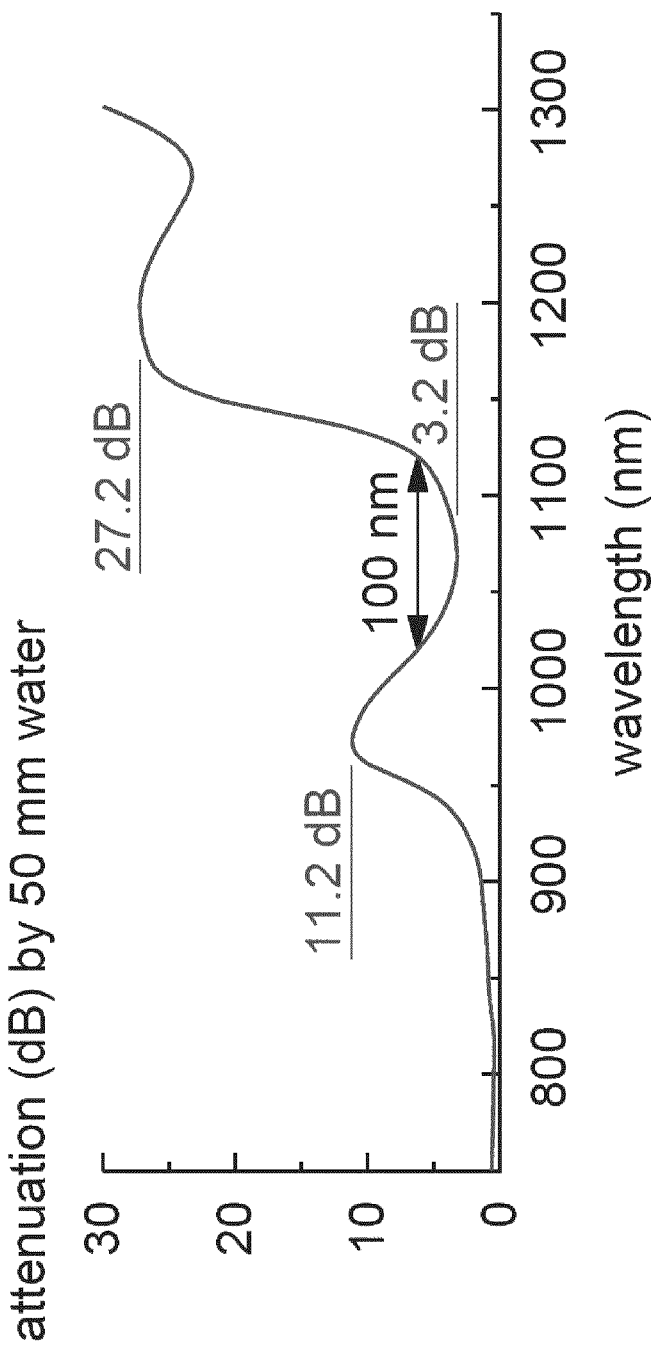
FIG. 1 is a graph illustrating the attenuation of light as a function of wavelength illustrating the minimum water absorption around 1060 nm wavelength range, which permits in vivo OCT imaging of the human retina.

The width of the 1060 nm water absorption window is a somewhat arbitrary dimension, as various levels of absorption may be deemed acceptable by the system designer. Marschall et al. found 100-120 nm of spectral bandwidth, centered close to water absorption minimum between 1060 nm-1070 nm, to be the maximum spectral bandwidth for imaging the human retina (see for example, S. Marschall, C. Pedersen, P. E. Andersen, "Investigation of the impact of water absorption on retinal OCT imaging in the 1060 nm range," Biomed. Opt. Express 3, 7, 1620-1631, 2012). They found that 120 nm spectral bandwidth causes less than 10% resolution degradation, which could be overcome by spectral shaping. However spectral shaping would transform the resolution loss into an additional 1 dB sensitivity caused by water absorption. Marschall et al. mainly investigated the amount of impact that water absorption has on the axial resolution, but did not describe in detail the trade-off between resolution and measurement sensitivity as the bandwidth increases. An alternative way of quantifying the width of the 1060 nm water absorption window, which takes into account the sensitivity loss with increasing bandwidth would be, for example, determining the wavelengths at which light gets attenuated twice as heavily as light with a wavelength close to the water absorption minimum between 1060 nm and 1070 nm. Using water absorption data published by K. F. Palmer et al. (see for example, K. F. Palmer and D. Williams, "Optical properties of water in the near infrared," J. Opt. Soc. Am., 64, 1107-1110, 1974), this results in a spectral width of 101 nm centered at 1069.5 nm (see also FIG. 1).

The switching between light with different spectral bandwidths can occur using a controller as discussed elsewhere herein. The controller may be part of the light source itself or may be a separate element of an OCT system, such as the OCT system of FIG. 2. The switching between light with different spectral bandwidths can be implemented in various ways. In one embodiment, the controller may simply adjust the amplitude of the wavelength tuning element of a swept source to increase or reduce the spectral bandwidth. In another embodiment, the tuning element may span the same spectral bandwidth for both imaging modes, however the controller only activates the gain element (e.g. a semiconductor optical amplifier) during a portion of the sweep in the retina imaging mode, but activates the gain medium during a longer portion of the sweep or during the entire sweep in the anterior segment mode.

Figure 3A:
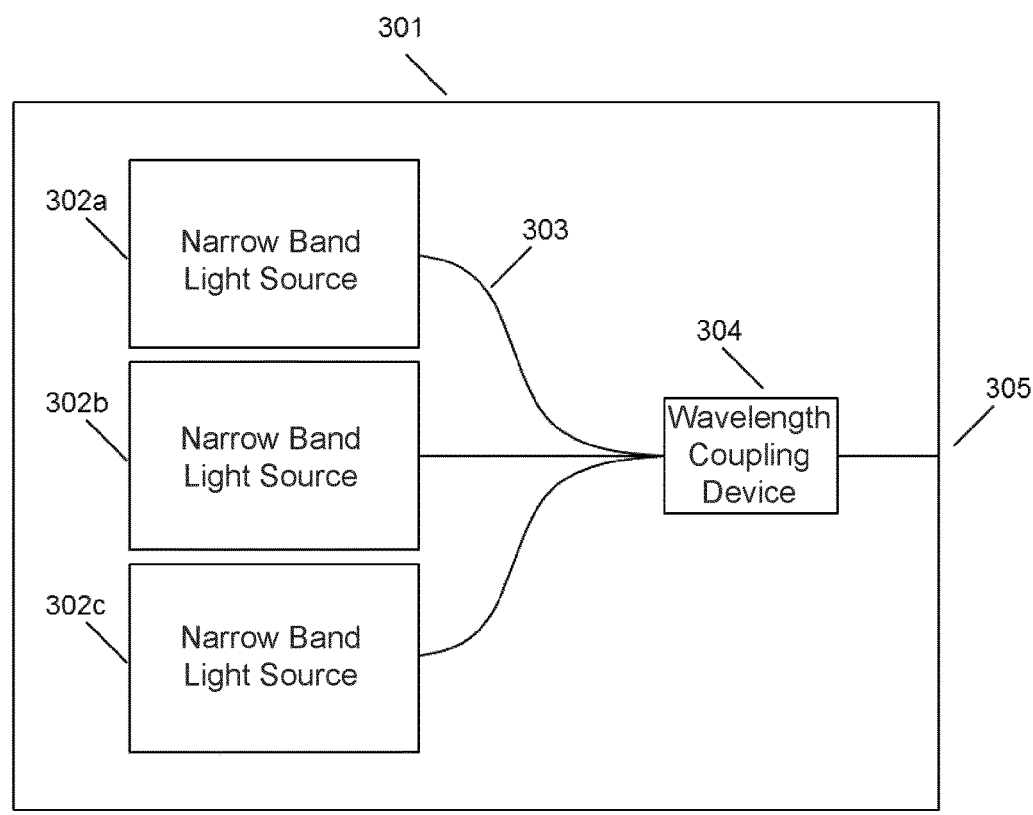
FIG. 3A illustrates an example embodiment of light source(s) that can be used with an OCT system for imaging the anterior/posterior segment of an eye.
Figure 3B:
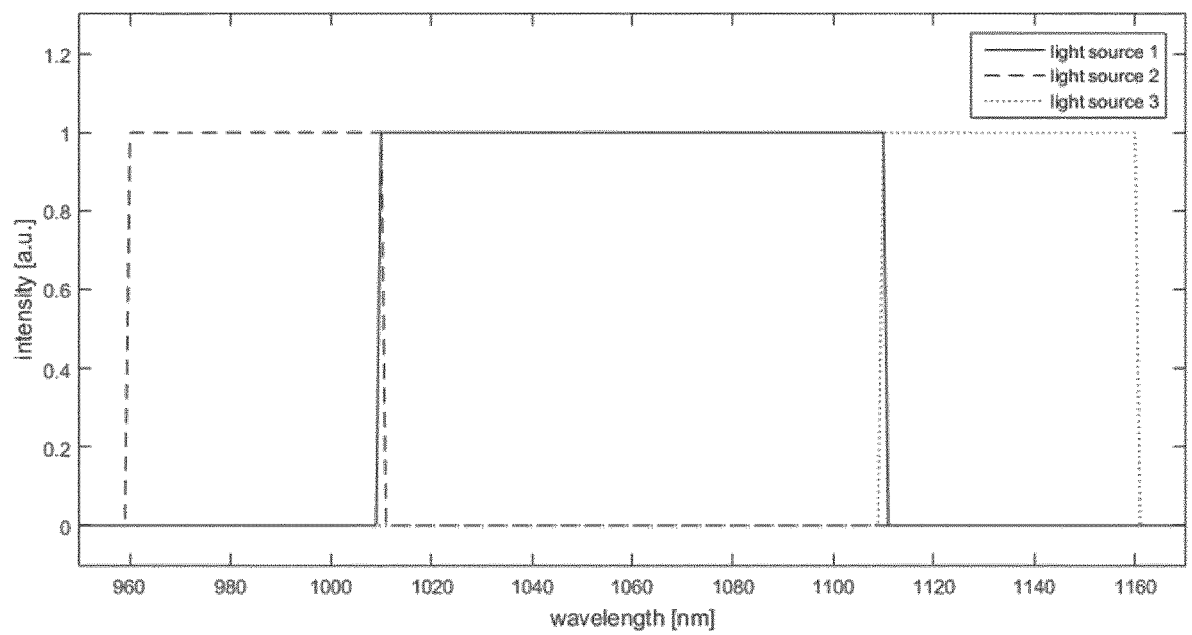
FIG. 3B shows the corresponding light intensity vs. wavelength plot for the light source(s) in FIG. 3A.

In yet another embodiment, as shown for example in FIG. 3A, a light source (301), which internally consists of multiple, spectrally complimentary, coupled narrower band light sources (302a-c) can be used. The individual narrow band light sources are illustratively coupled using an optical fiber (303) and a wavelength coupling device (304), which could consist, for example, of a wavelength division multiplexer, dichroic mirrors, fused fiber couplers, or a combination thereof. The light source (301) illustrated in FIG. 3A has a single fiber output (305). With such a light source, the controller would activate only a subset of the available internal light sources for retina imaging, but would choose to use more or all light sources, and therefore a larger spectral bandwidth, in a high resolution anterior segment mode. Someone with ordinary skill in the art of optical coherence tomography will recognize that the individual light sources do not have to reside within a single enclosure (301), but could be separately packaged light sources, coupled and operated in a similar fashion as described above. FIG. 3B shows an exemplary light intensity vs. wavelength plot for the three light sources discussed in FIG. 3A.

Figure 4A:
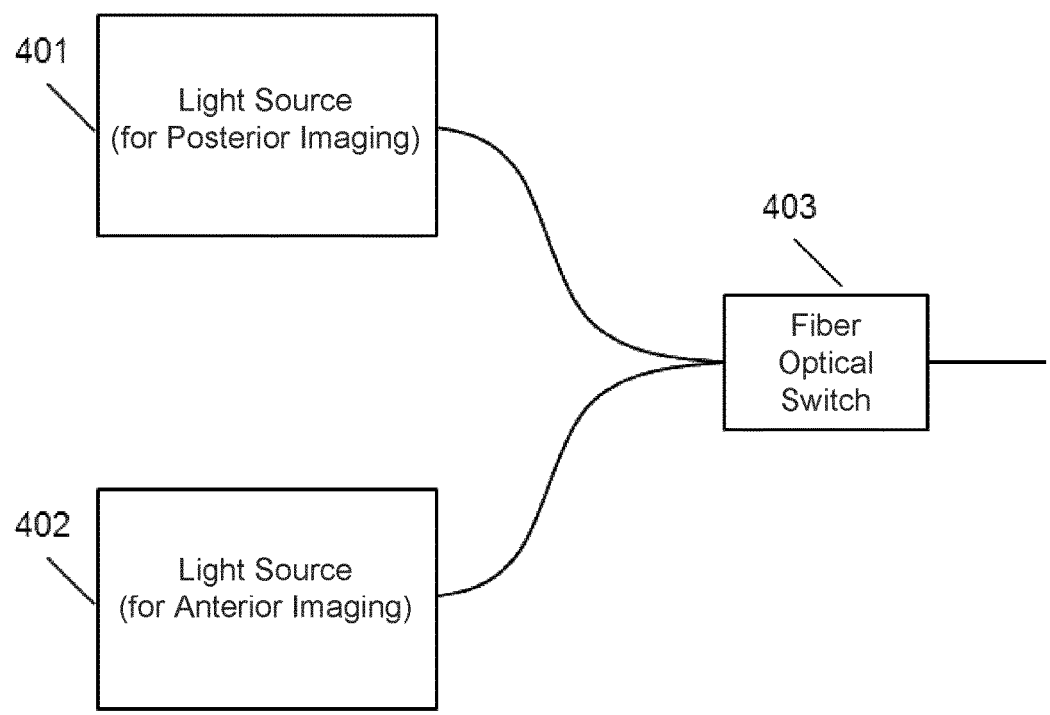
FIG. 4A illustrates another example embodiment of light source(s) that can be used with an OCT system for imaging the anterior/posterior segment of an eye.
Figure 4B:
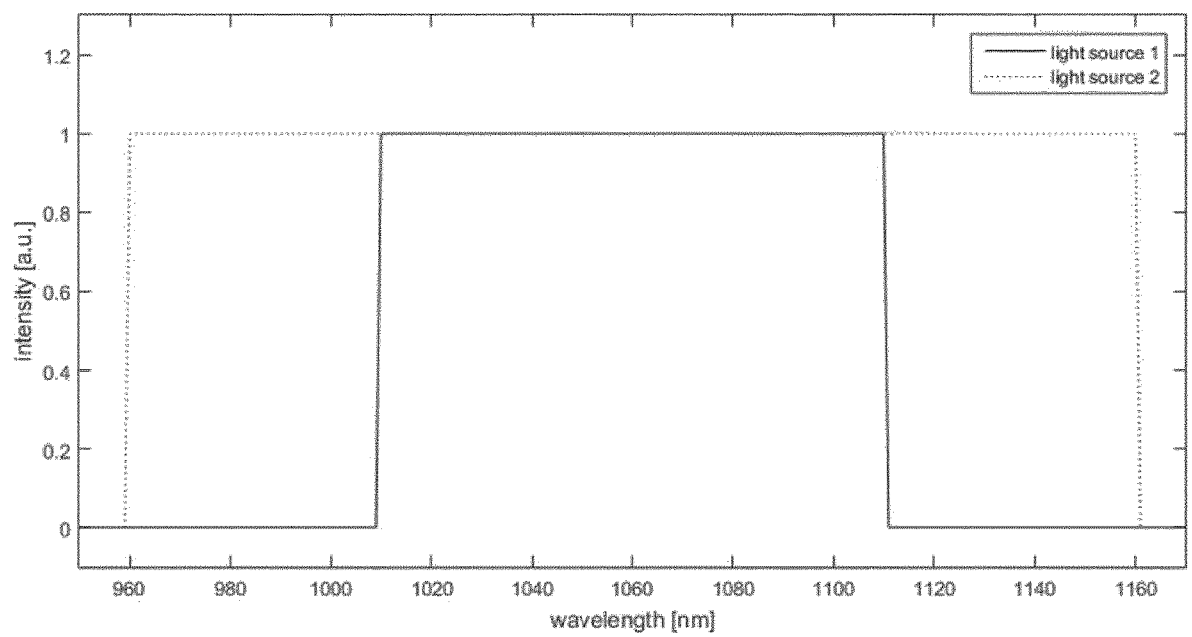
FIG. 4B shows the corresponding light intensity vs. wavelength plot for the light source(s) in FIG. 4A.

In yet another embodiment, as shown for example in FIG. 4A, the OCT system, may for example contain two separate light sources (401 & 402), which are partially spectrally redundant, i.e., one has a spectral range optimized for the 1060 nm water absorption window for imaging the posterior segment of the eye, and a second light source has a broader spectral range for imaging the anterior segment of the eye with higher resolution. Switching between light sources can for example be implemented with a fiber optical switch (403). FIG. 4B shows an exemplary light intensity vs. wavelength plot for the two light sources discussed in FIG. 4A.

The above-described embodiments involving multiple sources may be implemented with virtually any kind of light source suitable for OCT. In some instances, VCSELs or SG-DBR lasers may be particularly well suited due to their low cost laser cavity. This allows employing multiple laser cavities with different spectra, which share the same control electronics, without significantly impacting the cost of the complete light source.

Figure 5A:
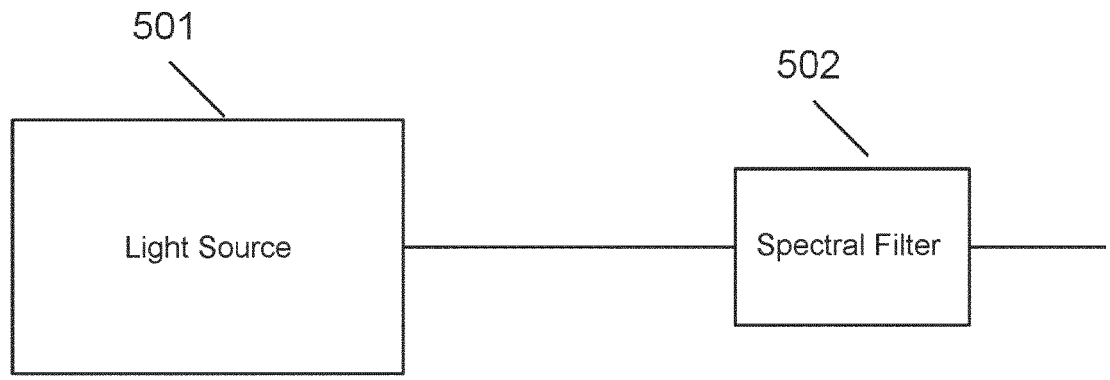
FIG. 5A illustrates another example embodiment of light source(s) that can be used with an OCT system for imaging the anterior/posterior segment of an eye.
Figure 5B:
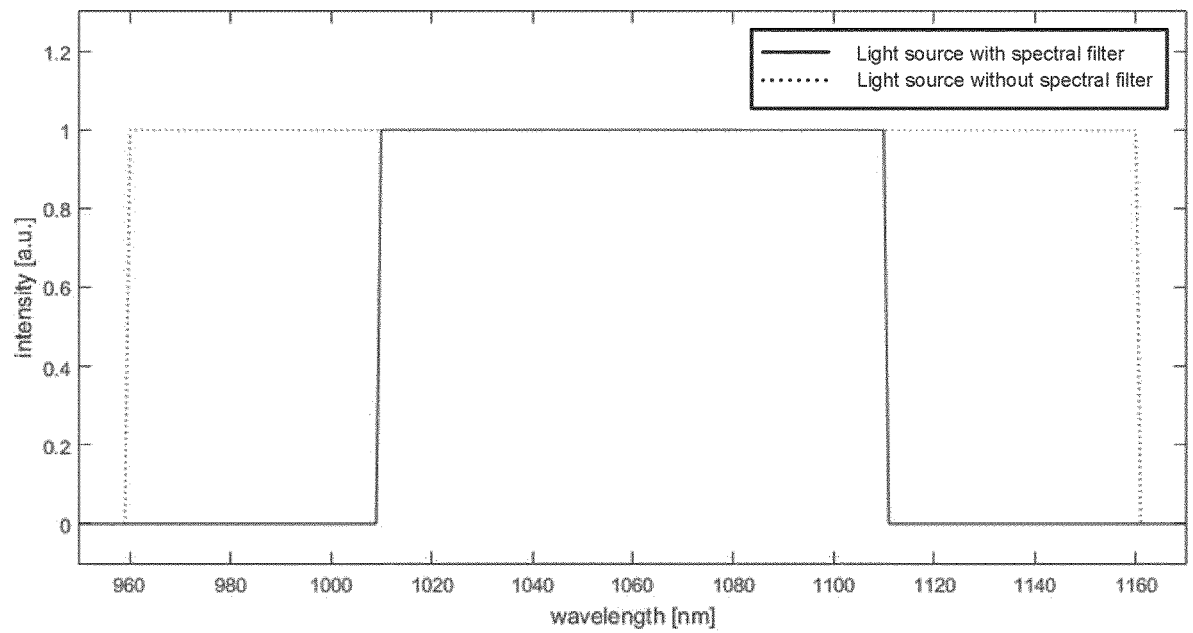
FIG. 5B shows the corresponding light intensity vs. wavelength plot for the light source(s) in FIG. 5A.

In yet another embodiment, as shown for example in FIG. 5A, the OCT system may use a light source (501), with a spectral bandwidth broad enough to cover at least the desired spectral band of the high resolution anterior segment mode. While the full bandwidth may be used for the anterior mode, in the retina imaging mode, the spectrum can be filtered (e.g., using the spectral filter (502)) to match the 1060 nm water absorption window. FIG. 5B shows an exemplary light intensity vs. wavelength plot for the light source with the spectral filter (for posterior imaging) and the light source without the spectral filter (for anterior imaging) discussed in FIG. 5A.

It should be understood that the invention is not limited to the above discussed embodiments and that a variety of other embodiments and/or configurations are also possible and within the scope of the present disclosure. Also, it should be understood that the light sources discussed with respect to the embodiments in FIGS. 3A-B, 4A-B, and 5A-B could be broadband light sources used with a spectrometer for detection or swept laser light sources. In a preferred embodiment of the present invention, these light sources are swept laser light sources.

Example Computer System

Figure 6:
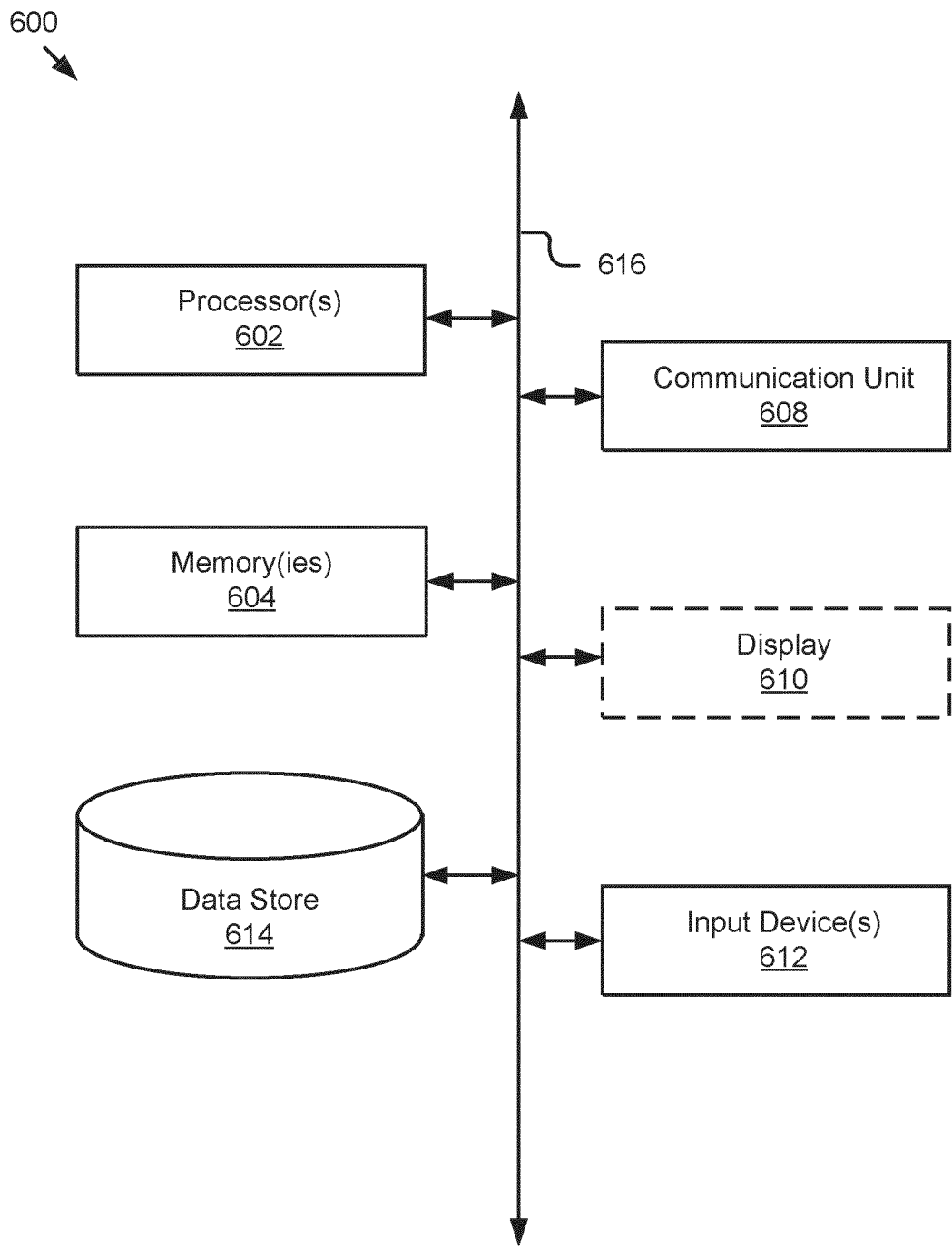
FIG. 6 is a block diagram of a general computer system that may perform the functions discussed in the disclosure according to one aspect of the present invention.

Unless otherwise indicated, the processing unit 221 that has been discussed herein (e.g., in reference to FIG. 2) may be implemented with a computer system configured to perform the functions that have been described herein for this unit. For instance, the processing unit 221 can be implemented with the computer system 600, as shown in FIG. 6. The computer system 600 may include one or more processors 602, one or more memories 604, a communication unit 608, an optional display 610, one or more input devices 612, and a data store 614. The display 610 is shown with dotted lines to indicate it is an optional component, which, in some instances, may not be a part of the computer system 600. In some embodiments, the display 610 is the display 222 that has been discussed herein in reference to FIG. 2.

The components 602, 604, 608, 610, 612, and 614 are communicatively coupled via a communication or system bus 616. The bus 616 can include a conventional communication bus for transferring data between components of a computing device or between computing devices. It should be understood that the computing system 600 described herein is not limited to these components and may include various operating systems, sensors, video processing components, input/output ports, user interface devices (e.g., keyboards, pointing devices, displays, microphones, sound reproduction systems, and/or touch screens), additional processors, and other physical configurations.

The processor(s) 602 may execute various hardware and/or software logic, such as software instructions, by performing various input/output, logical, and/or mathematical operations. The processor(s) 602 may have various computing architectures to process data signals including, for example, a complex instruction set computer (CISC) architecture, a reduced instruction set computer (RISC) architecture, and/or architecture implementing a combination of instruction sets. The processor(s) 602 may be physical and/or virtual, and may include a single core or plurality of processing units and/or cores. In some embodiments, the processor(s) 602 may be capable of generating and providing electronic display signals to a display device, such as the display 610, supporting the display of images, capturing and transmitting images, performing complex tasks including various types of feature extraction and sampling, etc. In some embodiments, the processor(s) 602 may be coupled to the memory(ies) 604 via a data/communication bus to access data and instructions therefrom and store data therein. The bus 616 may couple the processor(s) 602 to the other components of the computer system 600, for example, the memory(ies) 604, the communication unit 608, or the data store 614.

The memory(ies) 604 may store instructions and/or data that may be executed by the processor(s) 602. In some embodiments, the memory(ies) 604 may also be capable of storing other instructions and data including, for example, an operating system, hardware drivers, other software applications, databases, etc. The memory(ies) 604 are coupled to the bus 616 for communication with the processor(s) 602 and other components of the computer system 600. The memory(ies) 604 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor(s) 602. A non-transitory computer-usable storage medium may include any and/or all computer-usable storage media. In some embodiments, the memory(ies) 604 may include volatile memory, non-volatile memory, or both. For example, the memory(ies) 604 may include a dynamic random access memory (DRAM) device, a static random access memory (SRAM) device, flash memory, a hard disk drive, a floppy disk drive, a CD ROM device, a DVD ROM device, a DVD RAM device, a DVD RW device, a flash memory device, or any other mass storage device known for storing instructions on a more permanent basis.

The computer system for the processing unit 221 may include one or more computers or processing units at the same or different locations. When at different locations, the computers may be configured to communicate with one another through a wired and/or wireless network communication system, such as the communication unit 608. The communication unit 608 may include network interface devices (I/F) for wired and wireless connectivity. For example, the communication unit 608 may include a CAT-type interface, USB interface, or SD interface, transceivers for sending and receiving signals using Wi-Fi™; Bluetooth®, or cellular communications for wireless communication, etc. The communication unit 608 can link the processor(s) 602 to a computer network that may in turn be coupled to other processing systems.

The display 610 represents any device equipped to display electronic images and data as described herein. The display 610 may be any of a conventional display device, monitor or screen, such as an organic light-emitting diode (OLED) display, a liquid crystal display (LCD). In some embodiments, the display 610 is a touch-screen display capable of receiving input from one or more fingers of a user. For example, the device 610 may be a capacitive touch-screen display capable of detecting and interpreting multiple points of contact with the display surface.

The input device(s) 612 are any devices for inputting data on the computer system 600. In some embodiments, an input device is a touch-screen display capable of receiving input from one or more fingers of the user. The functionality of the input device(s) 612 and the display 610 may be integrated, and a user of the computer system 600 may interact with the system by contacting a surface of the display 610 using one or more fingers. In other embodiments, an input device is a separate peripheral device or combination of devices. For example, the input device(s) 612 may include a keyboard (e.g., a QWERTY keyboard) and a pointing device (e.g., a mouse or touchpad). The input device(s) 612 may also include a microphone, a web camera, or other similar audio or video capture devices.

The data store 614 can be an information source capable of storing and providing access to data. In the depicted embodiment, the data store 614 is coupled for communication with the components 602, 604, 608, 610, and 612 of the computer system 600 via the bus 616.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof. Furthermore, it should be understood that the modules, routines, features, attributes, methodologies and other aspects of the present subject matter can be implemented using hardware, firmware, software, or any combination of the three.

The invention claimed is:

1. An optical coherence tomography (OCT) system for generating images of an anterior or posterior segment of an eye, said system comprising:
   a light source for generating a beam of light, said light source capable of operating in at least two imaging modes comprising a posterior segment imaging mode in which the light source outputs light with a first spectral bandwidth of less than 120 nm and including wavelengths between about 1060 to 1070 nm, and an anterior segment imaging mode in which the light source outputs light with a second spectral bandwidth that is larger than 120 nm;
   a controller for switching between the posterior segment imaging mode and the anterior segment imaging mode;
   optics for scanning the generated light over a set of transverse locations across the anterior or posterior segment of the eye;
   a detector for measuring light returning from the eye and generating output signals in response thereto; and
   a processor for generating images of the anterior or posterior segment of the eye based on the output signals.

2. The OCT system as recited in claim 1, wherein said light source is a swept laser light source.

3. The OCT system as recited in claim 1, wherein said light source comprises multiple lasers coupled together to provide a spectral bandwidth broader than the spectral bandwidth of each individual laser.

4. The OCT system as recited in claim 1, wherein said light source comprises multiple lasers coupled together to provide a spectral bandwidth broader than the spectral bandwidth of each individual laser and the light source uses all individual lasers for anterior segment imaging mode and disables one or more lasers for the posterior segment imaging mode.

5. The OCT system as recited in claim 1, wherein said light source contains a tunable filter controlled by a drive function, which is modified to adjust the spectral bandwidth of the source.

6. The OCT system as recited in claim 1 wherein the first spectral bandwidth is centered between about 1060 to 1070 nm.

7. The OCT system as recited in claim 6 wherein the second spectral bandwidth is centered between about 1060 to 1070 nm.

8. An optical coherence tomography (OCT) system for generating images of an anterior or posterior segment of an eye, said system comprising:
   a light source for generating a beam of light, an adjustable spectral filter with a first spectral bandwidth for a posterior segment imaging mode, the first spectral bandwidth being less than 120 nm and including wavelengths between about 1060 to 1070 nm and a second spectral bandwidth that is larger than 120 nm for an anterior segment imaging mode;
   a controller for switching between the posterior segment imaging mode and the anterior segment imaging mode;
   optics for scanning the generated light over a set of transverse locations across the anterior or posterior segment of the eye;
   a detector for measuring light returning from the eye and generating output signals in response thereto; and
   a processor for generating images of the anterior or posterior segment of the eye based on the output signals.

9. The OCT system as recited in claim 8 wherein the first spectral bandwidth is centered between about 1060 to 1070 nm.

10. The OCT system as recited in claim 9 wherein the second spectral bandwidth is centered between about 1060 to 1070 nm.

11. An optical coherence tomography (OCT) system for generating images of an anterior or posterior segment of an eye, said system comprising:
    two light sources for generating beams of light, wherein the first light source has a first spectral bandwidth less than 120 nm and including wavelengths between about 1060 to 1070 nm for imaging the posterior segment of the eye, and the second light source has a second spectral bandwidth larger than 120 nm for imaging the anterior segment of the eye, and wherein said two light sources are coupled together;
    a controller for switching between the posterior segment imaging mode and the anterior segment imaging mode;
    optics for scanning the generated light beam for the selected imaging mode over a set of transverse locations across the anterior or posterior segment of the eye;
    a detector for measuring light returning from the eye and generating output signals in response thereto; and
    a processor for generating images of the anterior or posterior segment of the eye based on the output signals.

12. The OCT system as recited in claim 11, wherein the two light sources are coupled by an optical fiber switch.

13. The OCT system as recited in claim 11, wherein the two light sources are coupled by a fused fiber coupler.

14. The OCT system as recited in claim 11, wherein switching between light sources is done by switching the optical output of one light source on and the other off.

15. The OCT system as recited in claim 11 wherein the first spectral bandwidth is centered between about 1060 to 1070 nm.

16. The OCT system as recited in claim 15 wherein the second spectral bandwidth is centered between about 1060 to 1070 nm.

* * * * *

UNITED STATES PATENT AND TRADEMARK OFFICE
CERTIFICATE OF CORRECTION

PATENT NO. : 11,058,297 B2
APPLICATION NO. : 16/330355
DATED : July 13, 2021
INVENTOR(S) : Tilman Schmoll It is certified that error appears in the above-identified patent and that said Letters Patent is hereby corrected as shown below:

On the Title Page

On the page 2, in Column 2, under "Other Publications", Line 18, delete "um"," and insert -- µm", --, therefor.

Signed and Sealed this
Ninth Day of November, 2021

Drew Hirshfeld
*Performing the Functions and Duties of the
Under Secretary of Commerce for Intellectual Property and
Director of the United States Patent and Trademark Office*